US007399295B2

(12) United States Patent
Waldenburg

(10) Patent No.: US 7,399,295 B2
(45) Date of Patent: Jul. 15, 2008

(54) MEDICATION CAPSULE, SYRINGE USED WITH MEDICATION CAPSULE AND METHOD OF ADMINISTRATING MEDICATION

(76) Inventor: Ottfried Waldenburg, 8424 Amethyst La., Tucson, AZ (US) 85750-9707

( * ) Notice: Subject to any disclaimer, the term of this patent is extended or adjusted under 35 U.S.C. 154(b) by 0 days.

(21) Appl. No.: 11/526,142

(22) Filed: Sep. 22, 2006

(65) Prior Publication Data

US 2007/0073238 A1 Mar. 29, 2007

Related U.S. Application Data

(62) Division of application No. 10/253,394, filed on Sep. 24, 2002, now Pat. No. 7,112,188.

(60) Provisional application No. 60/324,678, filed on Sep. 25, 2001.

(51) Int. Cl.
*A61M 5/24* (2006.01)
(52) U.S. Cl. ........................ 604/201; 604/191
(58) Field of Classification Search ............. 604/87, 604/88, 89–92, 191, 218, 234, 200–207, 604/211, 56, 232
See application file for complete search history.

(56) References Cited

U.S. PATENT DOCUMENTS

| 213,978 | A | * | 4/1879 | Dibble | 604/183 |
| 1,950,137 | A | * | 3/1934 | Dowe | 604/30 |
| 5,078,691 | A | * | 1/1992 | Hamacher | 604/191 |
| 6,461,334 | B1 | * | 10/2002 | Buch-Rasmussen et al. | 604/230 |
| 6,692,468 | B1 | * | 2/2004 | Waldenburg | 604/191 |

* cited by examiner

*Primary Examiner*—Sharon E. Kennedy
(74) *Attorney, Agent, or Firm*—John J. Connors; Connors & Assoc. Inc

(57) ABSTRACT

A medical syringe employs a capsule containing multiple doses of medication within a sealed storage chamber formed between concentric inner and outer walls. The inner wall forms a cavity including a delivery chamber from which a single dose of medication is ejected. The syringe includes an ejection port, an axial moveable plunger extending into the cavity and delivery chamber, and a body with a compartment that holds the capsule. With the plunger in a first position, the capsule is closed. With the plunger in a second position, the delivery chamber is filled with a single dose of medication. With the plunger in a third position, the single dose of medication is ejected from the delivery chamber though the injection port.

6 Claims, 7 Drawing Sheets

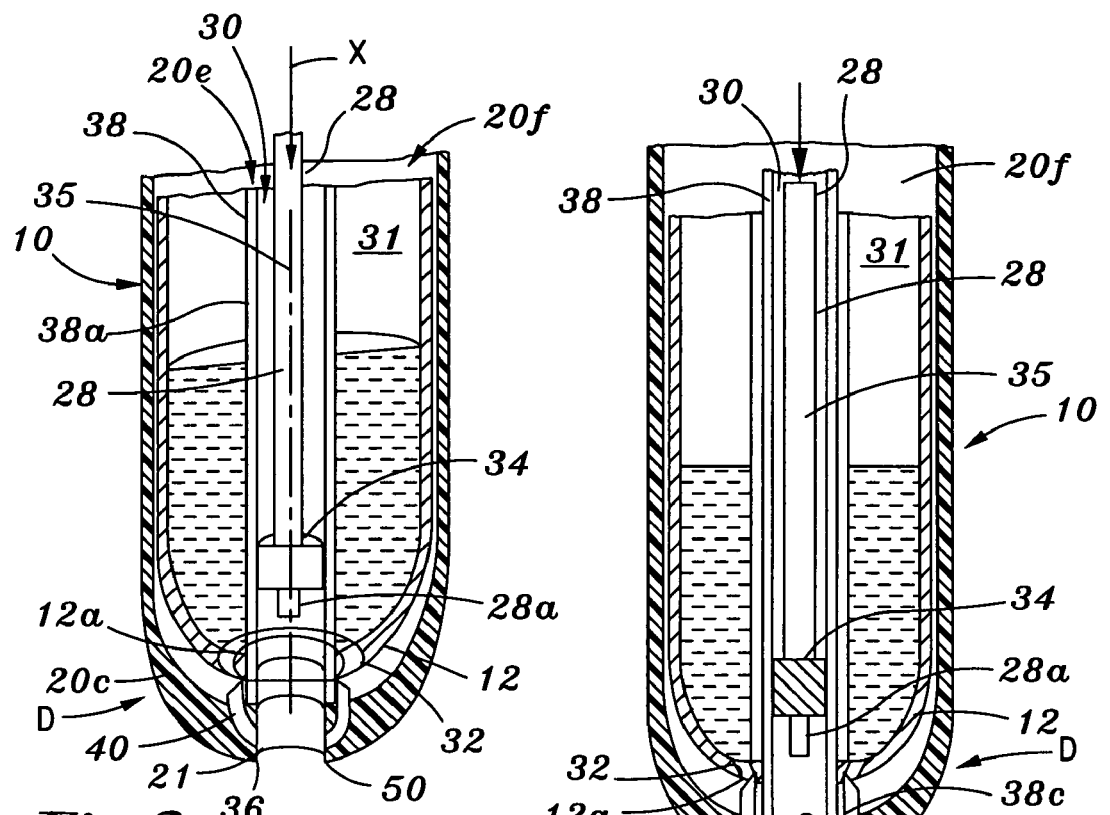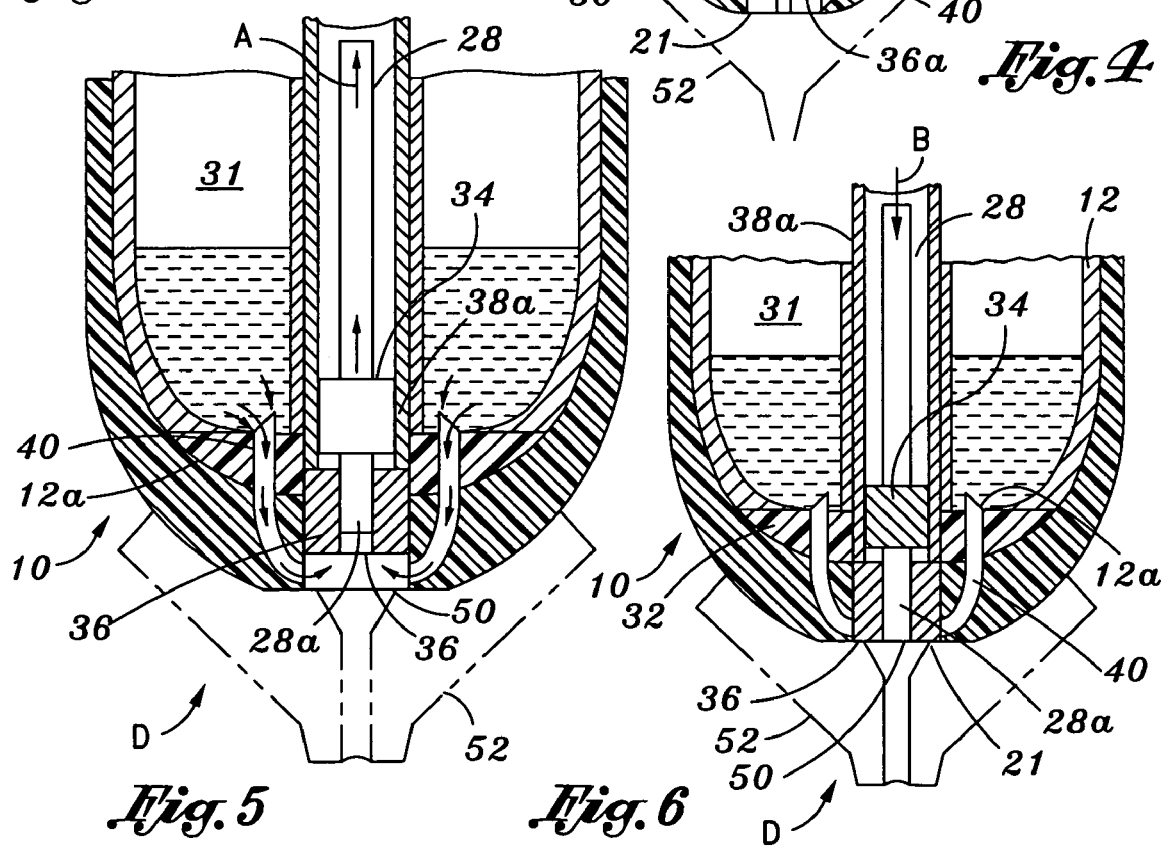

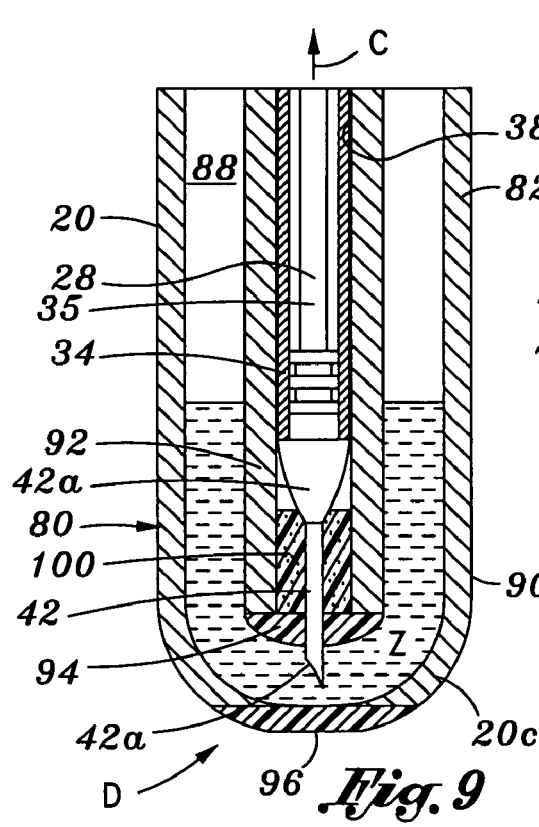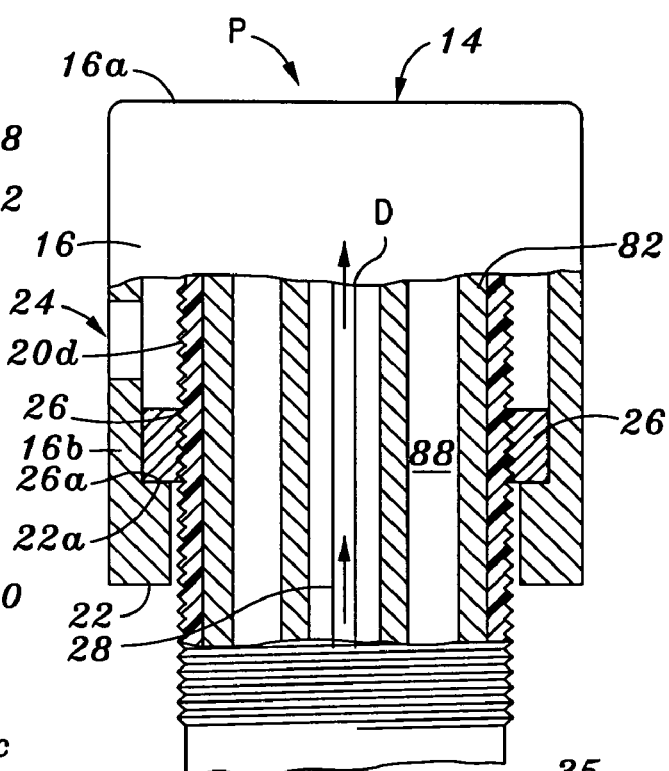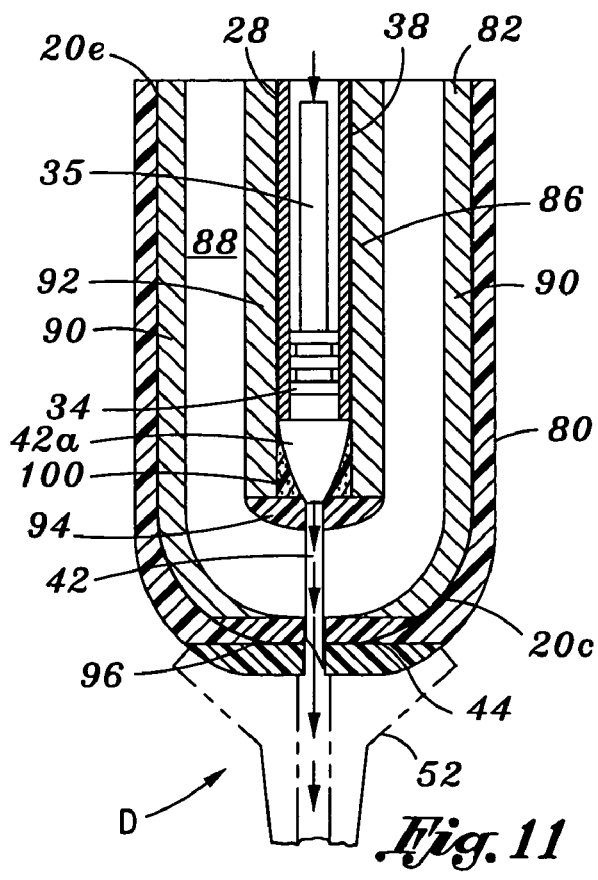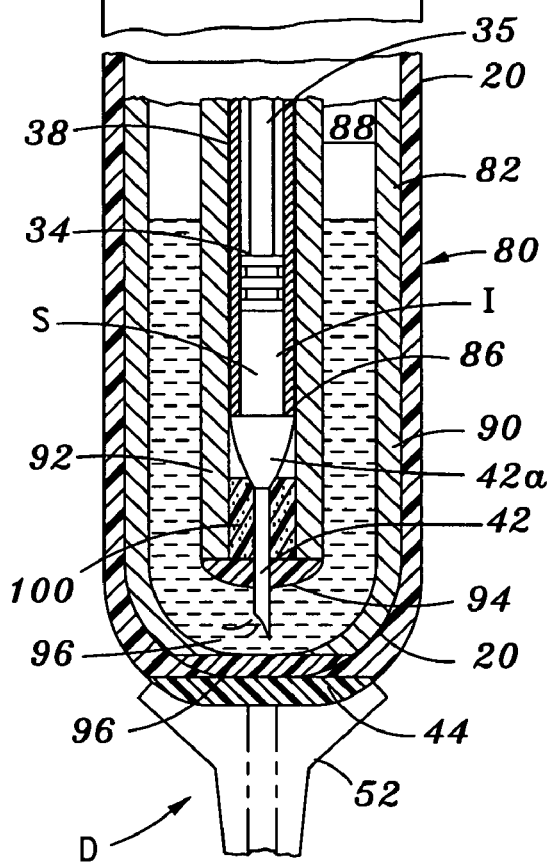
Fig. 9
Fig. 10
Fig. 11

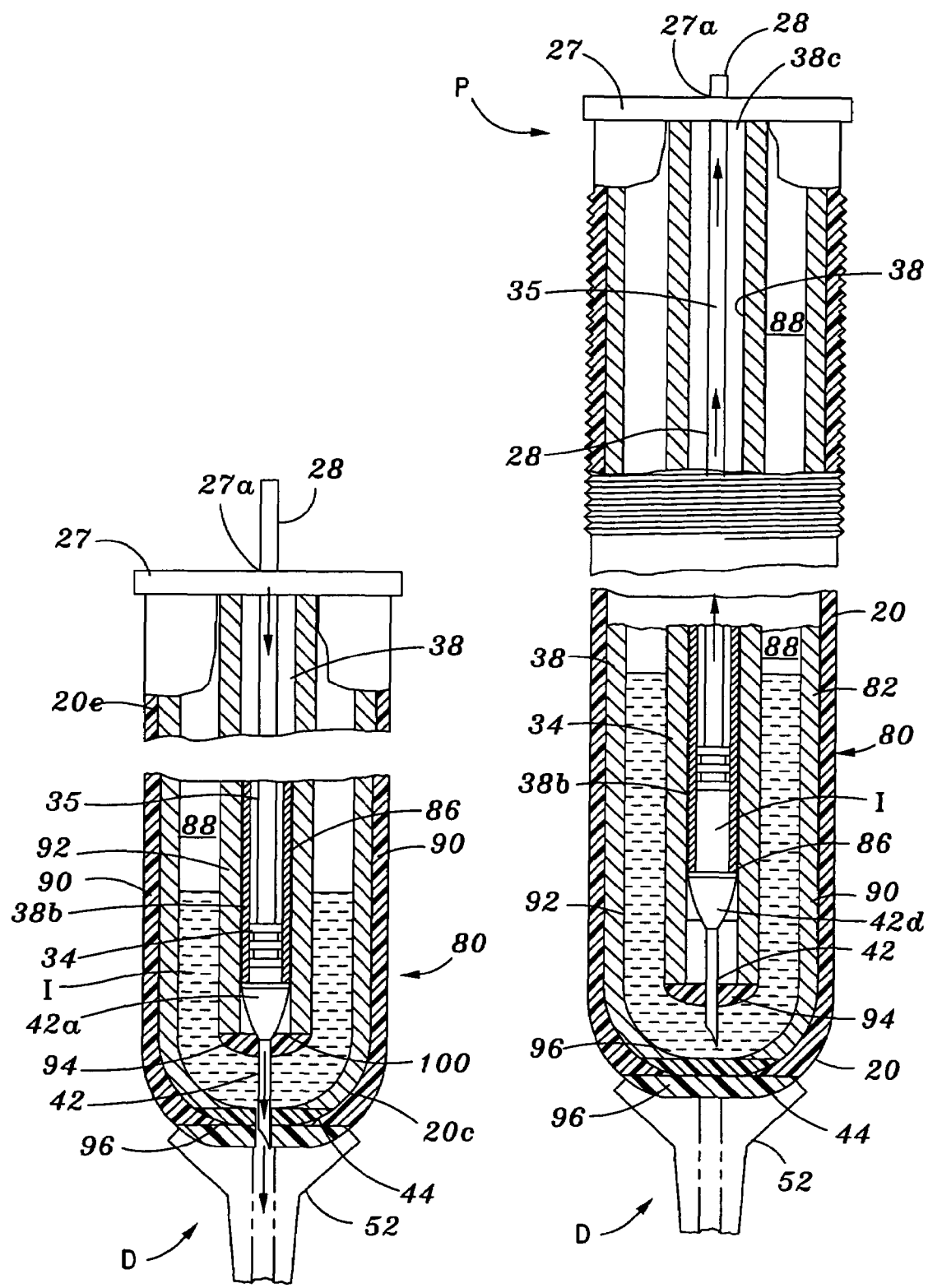

MEDICATION CAPSULE, SYRINGE USED WITH MEDICATION CAPSULE AND METHOD OF ADMINISTRATING MEDICATION

RELATED PATENT APPLICATIONS & INCORPORATION BY REFERENCE

This application is a divisional patent application of U.S. patent application Ser. No. 10/253,394 filed Sep. 24, 2002 (now U.S. Pat. No. 7,112,188, which in turn is a utility application which claims the benefit under 35 USC 119(e) of U.S. provisional patent application Ser. No. 60/324,678, entitled "Medication Capsule, Syringe With Medication Capsule & Method Of Administering Medication," filed Sep. 25, 2001. These related utility and provisional applications are incorporated herein by reference and made a part of this application. If any conflict arises between the disclosure of the invention in this divisional application and that in the related provisional application, the disclosure in this divisional application shall govern. Moreover, the inventor incorporates herein by reference any and all U.S. patents, U.S. patent applications, and other documents cited or referred to in this divisional application.

BACKGROUND OF THE INVENTION

In International Patent Application Number PCT/US95/12425 (herein the PCT application) the inventor disclosed his dual chamber syringe (herein First Syringe) having the many features and benefits stated in the PCT application. One feature of this First Syringe is a fluid reservoir holding multiple, single dosages of medication. Another feature is the fluid reservoir is accessible to a delivery chamber upon axial displacement of a plunger. It would be highly desirable to use these features in a syringe to deliver medication that is incompatible with the conventional plastic material used to manufacture syringes like the First Syringe. Insulin is one such medication. As will now be disclosed, the inventor has invented a novel, multi-dose capsule used with the syringe of this invention made of a plastic or plastics that are ordinarily incompatible with medications such as Insulin.

SUMMARY OF INVENTION

This invention includes (1) a medication capsule, (2) a syringe used with the medication capsule, and (3) a method of administrating medication, particularly insulin, The invention, with its several desirable features, is summarized and defined in the CLAIMS that follow. After reading the following section entitled "DETAILED DESCRIPTION," one skilled in the art will understand the benefits this invention provides. These benefits include, but are not limited to: (1) providing an easy to use, low cost, sterile and replaceable medication capsule, and (2) a syringe that is easy to assemble and is made of conventional materials and manufacturing technology.

This invention may be broadly viewed as a combination of a capsule and a syringe. The capsule is made of material that is compatible with long term storage therein of medication and contains multiple doses of the medication. The capsule includes a sealed wall portion that is opened upon assembly of the capsule and syringe, but its contents, the medication, e.g. Insulin, remain sterile. The syringe includes a body member that holds the capsule, a delivery chamber accessible to the medication in the capsule upon opening the sealed wall portion upon assembly of the body member and capsule, and a manually operable plunger member. The plunger member extends into a cavity in the capsule and also into the delivery chamber positioned within the cavity. The plunger member is axially displaceable therein to draw into the delivery chamber the single dose of medication upon displacement of the plunger member in one direction and to eject the single dose from the delivery chamber upon displacement of the plunger member in the opposite direction. Preferably, the capsule comprises a glass storage chamber holding such medication as Insulin. Glass is the material of choice in most instances because it is inert with respect to most medications. An injection port at the distal end of the syringe includes a detachable needle that is stuck into a patient when an injection of a single dose is administered. An optional feature is a dose meter for manually setting the amount of medication delivery with each single dose injection.

The plunger member is at a proximal end of the syringe and the ejection port is at a distal end of the syringe. When moved axially in the first direction, the medication in the capsule flows into the delivery chamber in response to a partial vacuum created upon displacement of the plunger member in the first direction a predetermined distance corresponding to a single dose of medication. The delivery chamber comprises a tube disposed in the cavity in the capsule. The plunger member extends into this tube and has a plunger seal thereon that contacts an inside wall of the tube and grips the tube to move it when the plunger moves. Outward axial plunger movement assists in creating the partial vacuum within the tube. The plunger member is axial moveable within the tube between a closed position preventing medication from flowing from the capsule into the tube, a fill position where a single dose of medication from the capsule is drawn into the tube, and an ejection position where the single dose is injected from the tube through the injection port.

This invention also includes a medication capsule. This capsule comprises a closed, sealed, and sterile storage chamber holding multiple doses of medication such as Insulin and a cavity. The storage chamber is formed between an outer wall member and an inner wall member that are co-axial and concentric, with the inner wall member forming at least a portion of the cavity. The sealed storage chamber has a seal at the distal end and a proximal end that closes and seals this storage chamber. The proximal end has an opening therein to provide access to the cavity. In one embodiment, the inner wall member has a first seal at a distal end forming a bottom of the cavity and an opening at a proximal end to provide access to the cavity. The outer wall opposite the first seal is spaced from this first seal and has therein an aligned second seal. The first and second seals are made of an inert, self-sealing elastomeric material. In another embodiment, the cavity comprises a central longitudinal passageway extending through the capsule. This passageway is formed by the inner wall member and has a tubular configuration with opposed open ends.

This invention also includes a method of administering medication. This method comprises:

(a) providing a syringe with a detachable needle that is detached and replaced with each injection, said syringe including a medication capsule comprising a storage chamber holding multiple doses of medication and a delivery chamber interactive with a plunger member that when moved in a first direction draws a single dose of medication into the delivery chamber and when moved in a second direction injects medication from the delivery chamber through the needle, (b) with the delivery chamber holding a single dose of medication, sticking the needle into the patient and moving the plunger in the second direction to inject the single dose into the patient, (c) removing the needle from the patient and detaching it from the syringe.

After each injection, the syringe is wiped with a disinfectant prior to attaching another needle to the syringe. Because of the combination of the syringe and unique capsule, wiping with disinfectant is facilitated.

DESCRIPTION OF THE DRAWING

The preferred embodiments of this invention, illustrating all its features, are depicted in the accompanying drawings, which are for illustrative purposes only. These drawings includes the following figures (Figs.), with like numerals indicating like parts:

FIG. 3 is a fragmentary perspective view, partially in cross-section, of the distal end of a first embodiment of the syringe of this invention shown in FIG. 12, depicting the capsule shown in FIG. 8 being inserted into a compartment of the syringe to open a seal at a distal end of the capsule to enable access to medication in a sealed storage chamber of the capsule.

FIG. 4 is a fragmentary, cross-sectional view similar to that of FIG. 3.

FIG. 5 is a fragmentary, cross-sectional view of the embodiment shown in FIG. 3, depicting the syringe's plunger being axially displaced from a closed position to a fill position.

FIG. 6 is a fragmentary, cross-sectional view similar to that of FIG. 4, depicting the plunger being moved from its fill position into its injection position.

FIG. 9 is fragmentary cross-sectional view of the distal end of the second embodiment of the syringe of this invention shown in FIG. 13, depicting its plunger in the closed position.

FIG. 10 is a cross-sectional view of the second embodiment of the syringe of this invention shown in FIG. 13, depicting its plunger in a fill position.

FIG. 11 is a fragmentary cross-sectional view of the distal end of the second embodiment of the syringe of this invention shown in FIG. 12, depicting the plunger in its injection position.

FIG. 14 is cross-sectional view showing a proximal end of a tubular member forming a portion of the syringe's deliver chamber engaging a closure top that acts as a stop to limit outward axial movement of the tubular member.

FIG. 15 is cross-sectional view showing the proximal end of the tubular member displaced inward from the closure top shown in FIG. 14 and its distal end with attached needle element engaging as a stop to limit inward axial movement of the tubular member.

DETAILED DESCRIPTION

Some Preferred Embodiments

Figure 7:
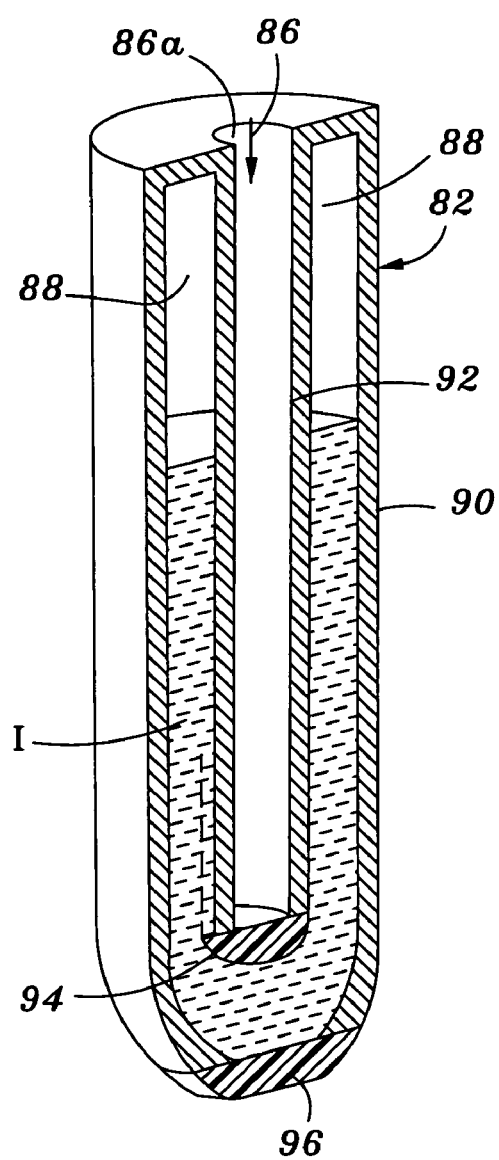
FIG. 7 is a perspective view with a section broken away of one embodiment of the capsule of this invention to be used with the embodiment of the syringe of this invention shown in FIG. 13.
Figure 8:
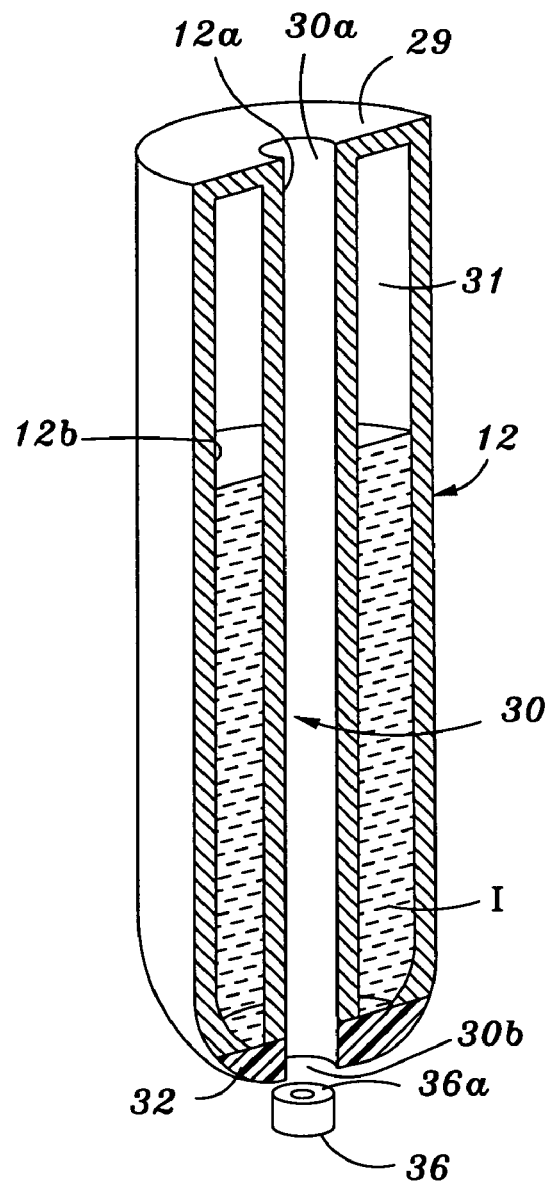
FIG. 8 is a perspective view with a section broken away of another embodiment of the capsule of this invention to be used with the embodiment of the syringe of this invention shown in FIG. 12.
Figure 12:
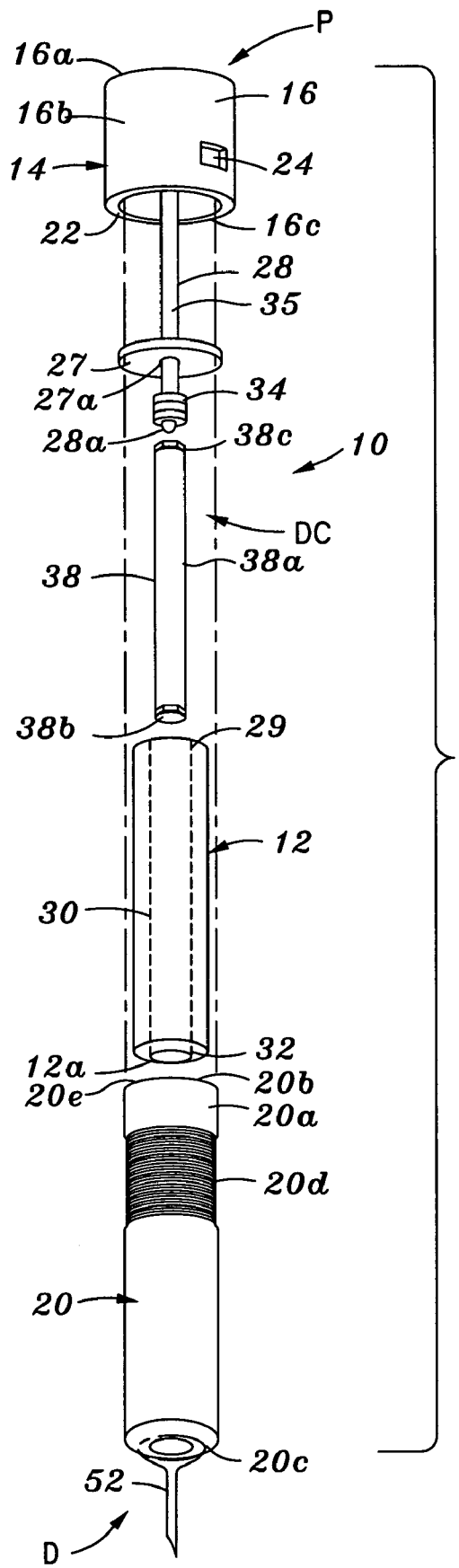
FIG. 12 is an exploded perspective view of the first embodiment of the syringe of this invention.
Figure 13:
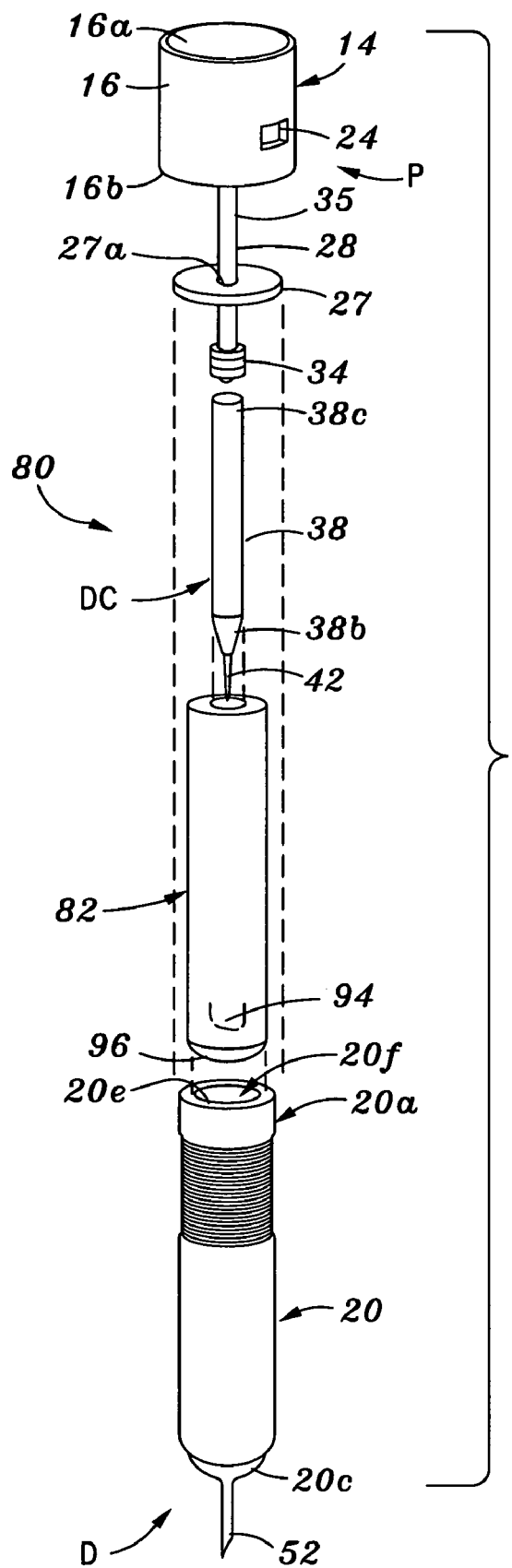
FIG. 13 is an exploded perspective view of the second embodiment of the syringe of this invention.

There are illustrated herein two embodiments of the syringe of this invention: the syringe 10 shown in FIG. 12 which uses the sealed capsule 12 shown in FIG. 8, and the syringe 80 shown in FIG. 13 which uses the sealed capsule 82 shown in FIG. 7. Each capsule 12 and 82 holds multiple, single doses. Each syringe 10 and 80 is capable of delivering a single dosage of medication I from its associated capsule 12 and 82 respectively to a delivery chamber DC including a tube 38 from which the single dose is expelled upon axial displacement of a plunger 28. The plunger 28 has at or near the distal end of its stem a seal plunger 34 fixedly attached to the stem. Typically, each capsule 12 and 82 contains from about 5 to about 15 milliliters of medication I to provide multiple, single dosages of medication I of from about 0.30 to about 0.60 milliliters per dose.

The capsules 12 and 82 are made of an material that is compatible with the medication I being delivered. In other words, the capsule material is inert with respect to the medication I. In the case of Insulin, the capsule material is glass and a self-sealing latex or rubber that is inert with respect to the Insulin. These capsules 12 and 82 are sterile when the medication I in placed therein and then sealed to prevent contamination. The seal is opened when a capsule is connected to a syringe 10 or 80, as the case may be. Both embodiments use an optional dose meter 14 and a body 20 for holding the capsules 12 and 82, as the case may be. This body 20 and the other components of the syringes 10 and 80 may be made of a plastic or other material that is incompatible with the medication I such as Insulin being delivered; provided this plastic or other material has no adverse effect when the Insulin makes momentary contact therewith as the Insulin flows through the delivery chamber DC upon axial displacement of the plunger 28.

Figure 1:
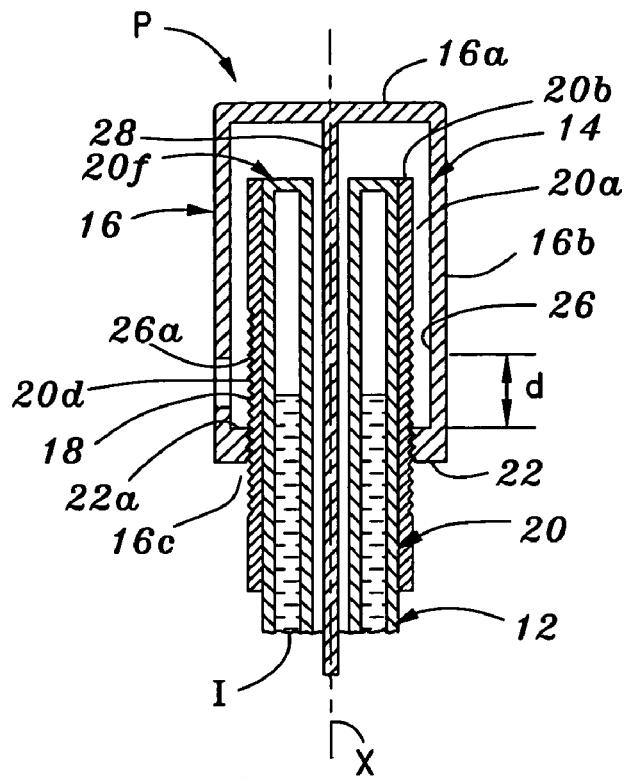
FIG. 1 is a cross-sectional view taken of the dose meter used with the syringe of this invention showing its cap disengaged from its control ring.

As subsequently discussed in greater detail, the plunger's distal end is interactive the delivery chamber DC to release a single dosage of medication I when the plunger 28 is moved axially towards the distal end D of the syringe 10 or 80, as the case may be. The plunger 28 acts in conjunction with the axial moveable tube 38 forming a portion of the delivery chamber DC that is disposed within the capsule 12 or 12, as the case may be. The tube 38 has a cylindrical side wall 38a, a distal end 38b and a proximal end 38c. In both syringes 10 and 80, the tube 38 has an open proximal end 38c. As shown in FIG. 1, the closed top end wall 16a of the cap 16 acts as a stop to limit the axial movement of the tube 38 in a direction towards a proximal end of the syringes 10 and 80, as the case may be. At this limit the open proximal end 38c of the tube abuts the inside surface of the top end wall 16a of the cap 16. As discussed subsequently in greater detail, the axial movement of the tube 38 in a direction towards a distal end of the syringes 10 and 80, as the case may be, is limited when the distal end 38b engages a portion of an associated capsule 12 or 82, as the case may be.

In the first embodiment, the syringe 10, a distal tip 28a of the plunger 28 is interactive with a plug 36 attached to a distal end 38b of the tube 38. In one position of the plunger 28, the distal tip 28a of the plunger fits into a hole 36a (FIGS. 6 and 8) in the plug 36 to block this hole. In the second embodiment, the syringe 80, there is a needle 42 at the distal end 38b of the tube 38. This needle 42 pierces a self-sealing seal 94 and a self-sealing seal 96 (FIGS. 9 and 11) in the capsule 82 as the plunger 28 is advanced towards the distal end D of the syringe 80. In both embodiments, the tube 38 is interactive with the seal plunger 34 as will be discussed subsequently in greater detail.

At a distal end 20c of the body 20 of both syringes 10 and 80 is an ejection port 50 with a detachable injection needle 52 connected to the body so that it may be removed after each injection of medication I and replaced with a new, sterile needle. This injection needle 52 is stuck into a patient when the medication I is to be delivered.

A Dose Meter

Figure 2:
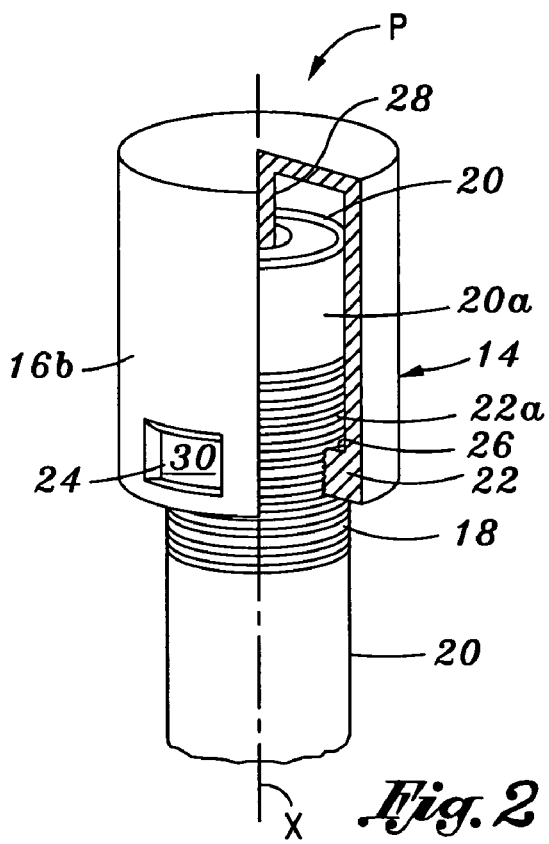
FIG. 2 is a fragmentary perspective view of the dose meter used with the syringe of this invention showing its cap engaging its control ring.

As depicted in FIGS. 1 and 2, each syringe 10 and 80 may use a manually operable dose meter 14. This is an optional feature, since the syringes 10 and 80 could be designed to deliver the same, single dose with each injection until the supply of medication I was depleted.

The dose meter 14 sets the amount of the single dosage of medication I delivered with each injection of medication. The dose meter 12 includes a cap 16 having a flat, closed top end wall 16a with a cylindrical side wall 16b projecting downward from this top end wall to form an open end 16c defined by an annular lip 22 having an inside threaded face 22a. The body 20 of each syringe 10 and 80 is a hollow, cylinder having external threads 20d near its proximal end 20a. This proximal end 20a is received within the open end 16c of the cap 16. The body 20 has a compartment 20f (FIG. 3) formed by a cylindrical side wall. When the cap 16 is removed, an open mouth 20e of the body's compartment 20f allows the capsule 12 or 82, as the case may be, to be manually inserted into the compartment 20f.

The cap 16 has a longitudinal axis that is co-extensive with a longitudinal axis X of the syringe 10 with the cap attached to the body 20 as shown in FIGS. 1 and 2. The cap 16 is axially and reciprocally manually moveable along the longitudinal axis X while attached to the body 20. This cap 20 has the proximal end of the stem 35 of the plunger 28 fixedly attached to the center of the top end wall 16a. As will be disclosed subsequently in greater, the plunger seal 34 near the tip 28a is interactive with the delivery chamber DC detail as the plunger 28 is moved from a closed position to a fill position to an injection position and finally returned to a closed position. The plunger 28 extends along the longitudinal axis X of the syringe 10 or 80 and it facilitates withdrawing from the capsule 12 or 82, as the case may be, a single dose of medication I after the capsule has been inserted into the compartment 20f of the body 20.

A closure top 27 is positioned to cover and close the open mouth 20e of the compartment 20f after the capsule 12 or 82 has been placed in the compartment. There is a central orifice 27a in the closure top 27 through which the stem 35 of the plunger 28 extends. This closure top 27 may be treaded on the body 20 so that it may be removed to replace a used capsule of medication I, or it may be fixedly attached by gluing or otherwise bonding to the body 20. In this later instance, the syringe 10 or 82, as the case may be, would not be reusable and therefore be discarded after the medication I in its associated capsule is exhausted.

Along the threaded proximal end 20a of the body 20 are indicium such as numbers corresponding to the amount of the single dosage to be delivered by the syringe 10 or 80, as the case may be. Typically, there is a series of numbers in a row parallel to the longitudinal axis X along the side wall of the body 20. Each number corresponds to a different amount of medication I to be delivered, i.e., the selected dosage amount. There is a window 24 in the side wall 16b and only one number, in this example the number 30, appears therein to indicate that the dose meter 12 is set to deliver a single dosage of 0.30 milliliters of medication I. This corresponds to the cap 16 and associated plunger 28 moving the axial distance d.

A threaded ring 26 engages the threads 20d on the proximal end 20a of the body member 20 and is manually rotated to preset the volume of the single dose to be delivered. It is advanced in an axial direction towards or away from the proximal end P of a syringe 10 or 80 as the case may be, depending on whether the ring 26 is rotated either clockwise or counter-clockwise. As illustrated in FIG. 2, the user first pulls the cap 16 outward towards the proximal end P of the syringe 10 or 82, as the case may be. This engages the inside thread 22a of the lip 22 of the cap 16 with a threaded underside 26a of the ring 26. With the lip 22 and ring 26 so engaged, the user rotates the ring by rotating the cap 16, changing the ring's relative position along the body 20 and repositioning the window 24 so that another number appears within this window. As shown in FIG. 1, with the ring 26 so positioned along the body 20, the cap 16 and its associated plunger 28 may only be moved outward axially a distance d before the lip 22 of the cap engages the ring 26. This axial movement of the plunger 28 results in medication I being drawn into the delivery chamber DC to fill this delivery chamber with a preset amount of medication corresponding to the distance d. This distance d may be varied to change the dosage volume by rotation of the ring 26 as explained above.

A First Embodiment

As illustrated in FIG. 8, the capsule 12 used with the syringe 10 has a generally cylindrical configuration formed by a pair of concentric cylindrical walls, inner wall 12a and outer wall 12b. The proximal end of the capsule 12 is closed by an annular wall 29. The inner wall 12a forms a cavity 30 that has open opposed ends 30a and 30b (FIG. 8) to provide a passageway that extends through the capsule 12 between its proximal and distal ends. The tube 38 is positioned within the cavity 30 with its longitudinal axis coextensive with a longitudinal axis of the cavity 30, which is coextensive with the axis X upon placing the capsule 12 in the compartment 20f. The tube 38 has its cylindrical wall 38a abutting the inner surface of the cylindrical wall 12a and, in response to the axial movement of the plunger 28, moves reciprocally and axially a few millimeters (mm), typically from about 2 to about 6 mm, within the cavity 30. At the distal end of the capsule 12 is a self-sealing seal 32 at least partially surrounding or enclosing the open end 30b of the cavity or passageway 30. Preferably this seal 32 is annular and encircles the open end 30b of the cavity 30. This capsule configuration provides a sealed storage chamber 31 that is initially essentially completely filled with enough medication I to provide multiple dosages. As medication is withdrawn from the storage chamber 31 with the administration of each single dose, air fills the space in this storage chamber corresponding to the volume of medication so withdrawn.

As best illustrated in FIGS. 3 through 6, and 12, the syringe 10 includes a pair of hallow, needle like piercing elements 40 to open the capsule 12 and release medication I. The piercing elements 40 are fixedly attached to the inside bottom of the compartment 20f and point upward into the compartment.

These piercing elements 40 are positioned to pierce the self-sealing seal 32 when the capsule 12 is forced to the bottom of the compartment 20f as shown in FIG. 6. Preferably, the piercing elements 40 are on opposite sides of the cavity 30. The piercing elements 40 pierce the seal 32 upon assembly of the components of the syringe 10.

In accordance with this first embodiment, the tube 38 forming the delivery chamber DC is lodged within the cavity 30. The tube 38 has a length slightly less than the length of the cavity 30 to allow the tube 38 to be moved axially within the cavity 30 after being placed in the capsule 12. The outward axial movement of the tube 38 terminates when its proximal end 38c engages the inside surface of the closure top 27. The inward axial movement of the tube 38 terminates when the plug attached to its distal end 38b engages the inside surface of the injection port 52. The attached plunger 28 moves axially when the cap 16 is moved axially, with plunger stem 35 freely moving through the orifice 27a in either an outward or an inward direction as the cap is moved in either such direction.

To assemble the syringe 10 and capsule 12, the tube 38 is positioned within the cavity 30 of the capsule and the capsule is placed in the open compartment 20f and forced inward towards the distal end 20c of the body to push the piercing elements 40 through the seal 32. The closure top 27 with the plunger stem 35 extending through the orifice 27a is then attached to the body 20 to close the open mouth 20e. The ring 26 is threaded on the body 20 and cap 16 without its end wall 16a slid over the ring 26 and then this end wall 16a is fixedly attached to the wall 16b. The plunger seal 34 fits snug within the tube 38 and grips this tube to move the tube axially with the axial movement of the plunger 28. The syringe 10 is now assembled as depicted in FIG. 6 with the plunger 28 in the closed position where the distal end 38 of the tube 38 with the attached plug 36 to its distal end 38b engaging the inside surface of the injection port 52. The tip 28a of the plunger 28 fits into the hole 36a in the plug 36.

Figure 5A:
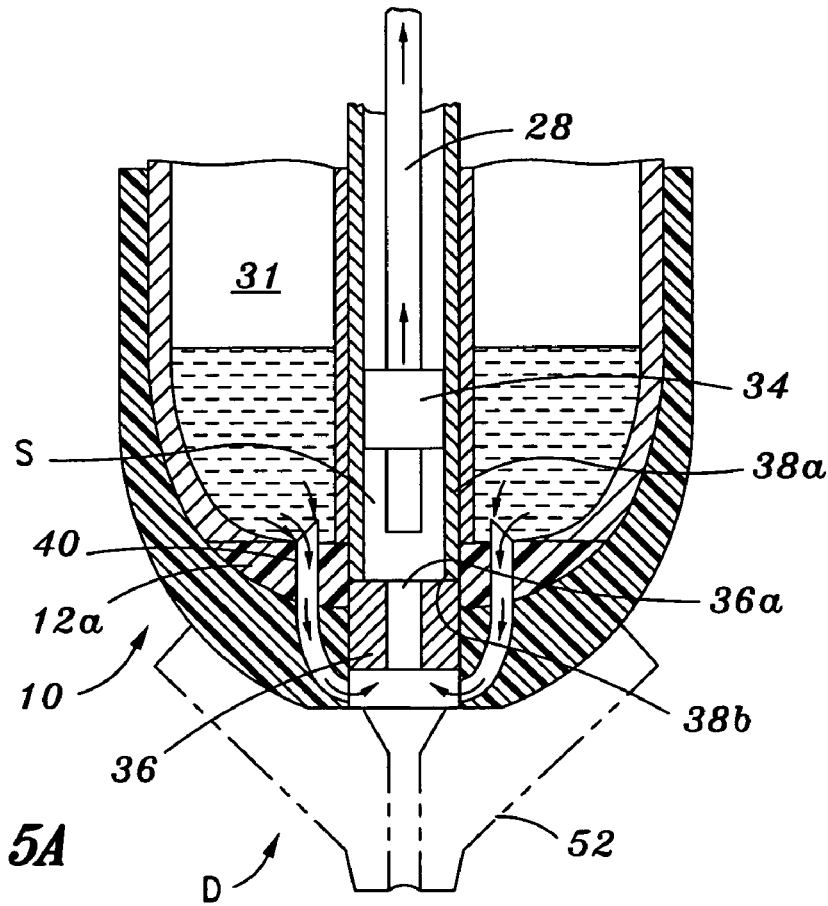
FIG. 5A is a fragmentary, cross-sectional view similar to that of FIG. 3, depicting the syringe's plunger in the fill position.

FIG. 5 shows the plunger 28 being initially advanced axially outward shown by the arrow A into its fill position shown in FIG. 5A. The tube 38 with the attached plug 36 first moves outward a slight distance sufficient to unblock the piercing elements 40 and allow medication I to flow from the capsule 12. When the proximal end 38c of the tube 38 engages the inside surface of the closure top 27, axial movement of the tube outwardly terminates. As the plunger 28 continues to move outwardly, the tip 28a of the plunger 28 is dislodged from the hole 36a in the plug 36. The medication I in the capsule 12 now flows into a space S created between the plunger seal 34 and the plug 36 as illustrated in FIG. 5A. With this movement of the plunger 28, there is a partial vacuum created in this space S that sucks the medication I into this space. The plunger 28 is moved axially outward until the lip 22 of the cap 16 contacts the ring 26. This is the fill position where the delivery chamber DC is filled with the preset dosage of medication I.

The plunger 28 expels the medication I from the space S through the hole 36a and out the injection port 50 and detachable 52 already stuck into a patient receiving the single dose of medication I by reversing the axial movement of the cap 16 and associated plunger 28. In other words, with the space S full of medication I and after sticking a patient with the needle 52, the plunger is moved from its fill position towards the proximal end 20b of the body 20 into its injection position shown in FIG. 6. The cap 16, including the plunger 28, is moved axially towards the ejection port 50 to push through the needle 52 the preset, single dose of medication I from the space S in the tube 28. The cap 16 is continued to be manually moved axially until its reaches the injection position shown in FIG. 6. The plunger seal 34 pushes medication I from the space S as the cap 16 advances towards the distal end 20c of the body 20, forcing the medication I out the injection port 50 and through the needle 52 into the patient.

The distal tip 28a of the plunger 28 serves as one component of a two-component connector and the plug 36 with its opening 36a serves as the second component of the two-component connector. The two components engage as shown in FIG. 6 and the plug 36 is moved into a position that blocks any flow of medication I through the piercing elements 40. In other words the closed position and the injection position are identical in this embodiment. This maintains the sterility of the medication I in the storage chamber 31.

With each injection, the needle 52 is detached and replaced with a new sterile needle 52. As shown in FIG. 6, the plug 36 is flush with the distal end 20c of the body 20 upon detaching the needle 52. This facilitates wiping the now exposed exterior surface of the plug 36 with alcohol or other disinfectant prior to attaching a new sterile needle 52 for a second injection of medication.

A Second Embodiment

Some of the principal differences between the syringe 80 and the syringe 10, is that the capsule 82 is used with the syringe 80, the syringe 80 eliminates of the piercing elements 40, and the tube 38 has a needle 42 with its hub 42a fixedly attached to the tube's distal end 38b. The needle 42 is coextensive with the longitudinal axis X when the cap 16 is attached to the body 20. The tube 38 is moved axially with the axial movement of the cap 16 in essentially the same manner as in the first embodiment of this invention. In the syringe 80, the distal end 20c of the body 20 has a self-sealing seal 44 thereat that is in alignment with the needle 42 and pierced by this needle when the needle 42 is advanced to the position shown in FIG. 11.

The capsule 82 has a generally cylindrical configuration with a longitudinal axis coextensive with the axis X when the capsule is placed in the compartment 20f. As shown best in FIG. 7, the capsule 82 has a centrally located cylindrical cavity 86 having an opening 86a in a proximal end. This cavity 86 is axially oriented along the longitudinal axis X with the capsule in the compartment 20f. The capsule 82 has a sealed storage chamber 88 containing multiple doses of medication I. The sealed storage chamber 88 is formed by a pair of spaced apart, opposed cylindrical walls 90 and 92. These walls 90 and 92 are concentric and have a longitudinal axis coextensive with the axis X upon connecting the capsule 82 to the body 20. Multiple doses of medication I are stored in the storage chamber 88 between these walls 90 and 92. The outer wall 90 has at its distal end a self-sealing seal 96 capable of being pierced by the needle 42 and the inner wall 92 has at its distal end another self-sealing seal 94 capable of being pierced by this same needle 42. The self-sealing seal 94 is located at or near a bottom of the cavity 86. The other self-sealing seal 96 forms the bottom of the capsule 82. These seals 94 and 96 are aligned but spaced apart to form between them the zone Z, and are along the X axis when the capsule 82 is placed in the syringe 80.

The syringe 80 and capsule 82 are assembled in essentially the same manner as discussed above in connection with the first embodiment, with the closure top 27 being attached after the capsule 82 is in the compartment 20f and the tube 38 is positioned within the cavity 86. In this embodiment, the needle 42 upon assembly of the syringe 80 and capsule 82 is pushed through the seal 94 into the medication I in the zone Z between the seals 94 and 96. This is the closed position as shown in FIG. 9. A resilient annular pad 100 is seated in the bottom of the cavity 86 in the capsule 82 and the needle 42 projects through this pad. As discussed above, the tube 38 is positioned within the cavity 86 so that it may move a few millimeters axially and reciprocally. The plunger seal 34 fits snug against the inside surface of the wall 38a of the tube 38. The plunger seal 34 grips the tube 38 and moves it outward or inward in response to the user manipulating the cap 16. The tube 38 moves outward until the proximal end 38c of the tube abuts the inside surface of the closure top 27 as shown in FIG. 14. The tube 38 moves inward until the hub 42a of the needle 42 abuts the seal 94 as shown in FIG. 11. The plunger seal 34 slides along the inside of the tube's wall 38a with axial movement of the cap 16 when the tube 38 is prevented from moving axially until the movement of the cap 16 stops outward plunger movement upon engaging the ring 26 or the hub 42a engages the seal 94 to stop inward plunger movement.

FIG. 9 depicts the plunger 28 in the closed position. Not until the plunger 28 is moved axially outward in the direction shown by the arrow D as shown in FIG. 14 will medication I in the capsule 82 be dawn into the space S by a vacuum created with such outward axial plunger movement. With continued outward axial movement of the plunger 28, the medication I flows from the zone Z through the needle 42 into the space S created in the tube 38. As discussed above, the setting of the dose meter 14 sets the dosage limiting the outward axial movement of the plunger to regulate the volume of the space S. The plunger 28 is moved outward until the ring 26 stops this movement. This is the fill position shown in FIG. 10.

As shown in FIG. 14, the plunger 28 is in the fill position and the needle 52 is stuck into a patient. The plunger 28 is then moved axially inward to advance the needle 42 into and through the seal 96 and seal 44. Continued inward advancement of the plunger 28, moves the plunger to the injection position shown in FIG. 15. The hub 42a of the needle 42 compresses the resilient annular pad 100 until completely compressed as shown in FIGS. 11 and 15. As the plunger 28 moves between the fill position to the injection position, the plunger seal 34 pushes the medication I in the space S in the tube 38 out the needle 42 and through the injection port 50 and out the needle 52 and into the patient. Upon release of the cap 16, the compressed the resilient annular pad 100 expands to return the plunger 28 to the closed position shown in FIG. 9. The needle 52 is now removed from the patient and detached from the syringe 80. Because the needle 42 has been withdrawn into the body 20 and is now in the position shown in FIG. 9, the seal 96 is exposed upon detaching the needle 52. This exposed seal 96 is wiped with alcohol or other disinfectant before attaching to the syringe 80 another sterile needle 52 for repeated use of the syringe 80 until the medication in the storage chamber 88 is exhausted.

SCOPE OF THE INVENTION

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover all modifications and alternate constructions coming within the spirit and scope of the invention as generally expressed by the following claims, which particularly point out and distinctly claim the subject matter of the invention:

The invention claimed is:

1. A medication capsule including
   a closed, sealed, and sterile storage chamber holding multiple doses of medication and including a cavity, said storage chamber formed between an outer wall member and an inner wall member that are co-axial and concentric, with the inner wall member forming at least a portion of the cavity,
   said storage chamber having a seal at the distal end and a proximal end that closes the storage chamber, said proximal end having an opening therein to provide access to the cavity.

2. A medication capsule including
   a closed, sealed, and sterile storage chamber including a central cavity and made of inert material,
   said storage chamber holding multiple doses of Insulin and formed between an outer cylindrical glass wall member and an inner cylindrical glass wall member that are co-axial and concentric, with the inner wall member forming at least a portion of the cavity,
   said inner wall member having a first seal at a distal end that forms a bottom of the cavity and an opening at a proximal end to provide access to the cavity, and
   said outer wall opposite the first seal being spaced from the first seal and having therein a second seal.

3. The inner wall member recited in claim 2 where the first and second seals are made of an inert, self-sealing elastomeric material.

4. A medication capsule including
   a closed, sealed, and sterile storage chamber made of inert material and including a central longitudinal passageway extending through the capsule,
   said storage chamber holding multiple doses of Insulin and formed between an outer cylindrical glass wall member and an inner cylindrical glass wall member that are co-axial and concentric, with the inner wall member having a tubular configuration with opposed open ends,
   a seal at the distal end of the capsule between distal ends of the inner and outer cylindrical glass wall members.

5. The inner wall member recited in claim 4 where the seal is made of an inert, self-sealing elastomeric material.

6. A medication capsule including
   a closed, sealed, and sterile storage chamber holding multiple doses of medication and having a central longitudinal axis,
   said storage chamber having a proximal end with a wall that closes and seals the proximal end of the storage chamber and a distal end with a seal that closes and seals the distal end of the storage chamber, said seal being adapted to be pierced by a needle like element to open the capsule and release medication from the storage chamber,
   said storage chamber being formed between an outer cylindrical wall member and an inner cylindrical wall member that are co-axial and concentric with the longitudinal axis and configured to form a substantially cylindrical cavity along the longitudinal axis that has an outer end that terminates in an opening that is surrounded by the proximal end of the storage chamber and a inner end terminating at or near the distal end of the storage chamber.

* * * * *